US011739311B2

(12) United States Patent
Guo et al.

(10) Patent No.: US 11,739,311 B2
(45) Date of Patent: Aug. 29, 2023

(54) GENE RECOMBINANT VECTOR, GENETICALLY ENGINEERED STRAIN AND PREPARATION METHOD OF COLLAGENASE

(71) Applicant: INSTITUTE OF FOOD SCIENCE AND TECHNOLOGY, CHINESE ACADEMY OF AGRICULTURAL, Beijing (CN)

(72) Inventors: Yujie Guo, Beijing (CN); Chunhui Zhang, Beijing (CN); Xia Li, Beijing (CN); Hongru Zhang, Beijing (CN)

(73) Assignee: INSTITUTE OF FOOD SCIENCE AND TECHNOLOGY, CHINESE ACADEMY OF AGRICULTURAL SCIENCES, Beijing (CN)

( * ) Notice: Subject to any disclaimer, the term of this patent is extended or adjusted under 35 U.S.C. 154(b) by 0 days.

(21) Appl. No.: 17/932,184

(22) Filed: Sep. 14, 2022

(65) Prior Publication Data
US 2023/0140307 A1 May 4, 2023

(30) Foreign Application Priority Data
Nov. 3, 2021 (CN) .......................... 202111291737.X

(51) Int. Cl.
*C12N 9/60* (2006.01)
*C12N 15/81* (2006.01)

(52) U.S. Cl.
CPC .............. *C12N 9/60* (2013.01); *C12N 15/815* (2013.01); *C12Y 304/24003* (2013.01); *C12N 2800/102* (2013.01)

(58) Field of Classification Search
CPC ...................................................... C12N 9/60
See application file for complete search history.

(56) References Cited

FOREIGN PATENT DOCUMENTS

| CN | 109971657 A | 7/2019 |
| CN | 111187692 A | 5/2020 |

OTHER PUBLICATIONS

Studer. Residue mutations and their impact on protein structure and function: detecting beneficial and pathogenic changes. Biochem. J. (2013) 449, 581-594.*
Freije. Molecular Cloning and Expression of Collagenase-3, a Novel Human Matrix Metalloproteinase Produced by Breast Carcinomas. The Journal of Biological Chemistry. vol. 269, No. 24, Issue of Jun. 17, pp. 16766-16773, 1994.*
Wang Rui et al, Isolation and purification of caseinase and collagenase from commercial bacillus subtilis AS1.39 enzyme by affinity chromatography Journal—Society of Leather Technologists and Chemists (vol. 93, No. 11) p. 1-9, Feb. 28, 2009.

* cited by examiner

*Primary Examiner* — Yong D Pak
(74) *Attorney, Agent, or Firm* — CBM Patent Consulting, LLC

(57) ABSTRACT

The present disclosure relates to a gene recombinant vector of a collagenase, comprising a collagenase gene, wherein an amino acid sequence of a collagenase encoded by the collagenase gene is shown in SEQ ID NO. 1; moreover, a genetically engineered strain of the collagenase and a preparation method of the collagenase are also disclosed; and the collagenase prepared according to the invention is capable of degrading a bone collagen, and improving a yield of a low-molecular-weight bone collagen peptide.

5 Claims, 3 Drawing Sheets
Specification includes a Sequence Listing.

SEQUENCE LISTING

```
Sequence total quantity: 6
SEQ ID NO: 1          moltype = AA  length = 397
FEATURE               Location/Qualifiers
source                1..397
```

```
                              mol_type = protein
                              organism = Rhizopus oryzae
SEQUENCE: 1
MKFTLVSSCV   ALVVMALSVE   AAPNGKKLSI   ALKQNTEYKP   SAPAAVAKAI   AKYQKHAINP    60
LKNTPSGSSS   TEGTGVVPVT   DYGNDIEYYG   DVQIGTPPQN   FKINFDTGSS   DLWVASTLCA   120
SCTSHTRYNP   NKSSTYVKDG   RPWSISYGDG   STASGILAYD   TVTLGGLAIK   KQTIELAQKE   180
SSSFASDPID   GLLGLGFNTI   TTVRGIKTPV   DNLISQGLIT   SPIYGVSLGK   ASNGGGGEYL   240
FGGYNKSKFT   GTLKTVPVDN   SQGFWGITVS   DLKVGTKSYG   TFDGILDTGT   TLLLFPTAYA   300
NKVATAYGAT   ANGDGTYNIN   CNTSGFKPLE   FTINGATFYV   PTNSLIFQKS   GSRCYASFGS   360
SNIPFAILGD   TFLKNNYVVF   NQQVPEVQIA   ASVDQNK                                397

SEQ ID NO: 2              moltype = DNA    length = 1252
FEATURE                   Location/Qualifiers
source                    1..1252
                          mol_type = other DNA
                          organism = Rhizopus oryzae
SEQUENCE: 2
atgaaattca ctcttgtctc ttcttgtgtg gcactggttg tcatggctct ttctgttgaa     60
gcagctccta atggcaagaa actttccatt gctttaaagc aaaatactga atacaagcct    120
agtgctcccg ctgctgttgc aaaggccatt gccaagtatc aaaagcatgc tattaatcct    180
ctcaaaaaca ctccttctgg atcttcctct actgaaggta ctggtgttgt acctgtcact    240
gattacggaa atgatattga atattacggt gatgttcaaa tcggtactcc tcctcaaaac    300
ttcaagatta actttgatac cggttcctcc gatttatggg ttggtaagta caattctctt    360
tttttgttta aaatattata taactaaaact attattatta gcctctactt tgtgtgcttc    420
ttgtaccagt catactcgtt acaatcccaa caaatcaagc acttatgtca aggatggtcg    480
tccatgtct atctcttacg gtgatggatc tactgctagc ggtattttag cttacgatac    540
tgttacttta ggtggccttg ctatcaagaa acaaacatt gaattagctc aaaaagaatc    600
cagcagtttc gcttctgatc ctattgatgg tcttctcggt cttggtttca ataccattac    660
cactgttaga ggtatcaaga ctcctgttga taacttgatc agtcaaggtt taattacttc    720
tcctatttat ggtgtttctc tcggtaaggc cagcaatggt ggaggtggtg aaatacctct    780
tggtggttac aataagtcca agttcactgg tactttaaag actgttcctg ttgataactc    840
tcaaggtttc tggggtatta ctgtcagtga tcttaaggtt ggtaccaaga gctatggtac    900
tttcgatggc atccttgata ccggtaccac tctttttactt tccctactg cctatgccaa    960
caaggtcgcc actgttatg gtgctactgc taatggtgat ggtacttaca acatcaactg   1020
taacacttct ggtttcaagc ctcttgaatt cactatcaat ggtgctactt tctatgttcc   1080
taccaactct ttgatcttcc aaaagagtgg atccagatgt tatgcttcat tcggttcatc   1140
caacattcct ttcgctattc ttggtgatac ttttcttgaag aacaactatg ttgtattcaa   1200
ccaacaagtc cctgaagttc aaatcgctgc ttctgttgac aaaacaaat aa             1252

SEQ ID NO: 3              moltype = DNA    length = 58
FEATURE                   Location/Qualifiers
source                    1..58
                          mol_type = other DNA
                          organism = Rhizopus oryzae
SEQUENCE: 3
gtaagtacaa ttctcttttt ttgtttaaaa tattatataa ctaaactatt attattag       58

SEQ ID NO: 4              moltype = DNA    length = 1194
FEATURE                   Location/Qualifiers
source                    1..1194
                          mol_type = other DNA
                          organism = Rhizopus oryzae
SEQUENCE: 4
atgaaattca ctcttgtctc ttcttgtgtg gcactggttg tcatggctct ttctgttgaa     60
gcagctccta atggcaagaa actttccatt gctttaaagc aaaatactga atacaagcct    120
agtgctcccg ctgctgttgc aaaggccatt gccaagtatc aaaagcatgc tattaatcct    180
ctcaaaaaca ctccttctgg atcttcctct actgaaggta ctggtgttgt acctgtcact    240
gattacggaa atgatattga atattacggt gatgttcaaa tcggtactcc tcctcaaaac    300
ttcaagatta actttgatac cggttcctcc gatttatggg ttgcctctac tttgtgtgct    360
tcttgtacca gtcatactcg ttacaatccc aacaaatcaa gcacttatgt caaggatggt    420
cgtccatggt ctatctctta cggtgatgga tctactgcta gcggtatttt agcttacgat    480
actgttactt taggtggcct tgctatcaag aaacaaacta ttgaattagc tcaaaaagaa    540
tccagcagtt tcgcttctga tcctattgat ggtcttctcg gtcttggttt caataccatt    600
accactgtta gaggtatcaa gactcctgtt gataacttga tcagtcaagg tttaattact    660
tctcctattt atggtgtttc tcggtaag gccagcaatg gtggaggtgg tgaatacctc    720
tttggtggtt acaataagtc caagttcact ggtactttaa agactgttcc tgttgataac    780
tctcaaggtt tctggggtat tactgtcagt gatcttaagg ttggtaccaa gagctatggt    840
actttcgatg gcatccttga taccggtacc actctttttact ttccctactg cctatgcc    900
aacaaggtcg ccactgttat ggtgctact gctaatggta tggtacttat caacatcaac    960
tgtaacactt ctggtttcaa gcctcttgaa ttcactatca atggtgctac tttctatgtt   1020
cctaccaact ctttgatctt ccaaaagagt ggatccagat gttatgcttc attcggttca   1080
tccaacattc ctttcgctat tcttggtgat acttttcttga agaacaacta tgttgtattc   1140
aaccaacaag tccctgaagt tcaaatcgct gcttctgttg accaaaacaa ataa           1194

SEQ ID NO: 5              moltype = DNA    length = 30
FEATURE                   Location/Qualifiers
source                    1..30
                          mol_type = other DNA
                          organism = synthetic construct
```

```
SEQUENCE: 5
cggaattcat gaaattcact cttgtctctt                                       30

SEQ ID NO: 6            moltype = DNA  length = 34
FEATURE                 Location/Qualifiers
source                  1..34
                        mol_type = other DNA
                        organism = synthetic construct
SEQUENCE: 6
ttgcggccgc ttatttgttt tggtcaacag aagc                                  34
```

GENE RECOMBINANT VECTOR, GENETICALLY ENGINEERED STRAIN AND PREPARATION METHOD OF COLLAGENASE

REFERENCE TO AN ELECTRONIC SEQUENCE LISTING

The contents of the electronic sequence listing (220925.xml; Size: 9,060 bytes; and Date of Creation: Sep. 14, 2022) is herein incorporated by reference in its entirety.

TECHNICAL FIELD

The present disclosure relates to the field of biotechnologies. More particularly, the present disclosure relates to a gene recombinant vector, a genetically engineered strain and a preparation method of a collagenase.

BACKGROUND

Bones of livestock and poultry are rich in bone collagen, which is an important raw material for preparing a functional bone collagen peptide, and has a great value in use. A low-molecular-weight bone collagen peptide prepared by enzymolysis of the bone collagen of livestock and poultry has the activities of anti-oxidation, anti-aging, mineral absorption promotion and anti-osteoporosis. Meanwhile, the low-molecular-weight bone collagen peptide has the characteristics of good solubility and easy absorption, and has a better absorption effect than that of a collagen. At present, protease hydrolysis is the most commonly used method for preparing the low-molecular-weight bone collagen peptide, and has the advantages of low cost, simple operation and mild condition. However, due to unique (G-X-Y) n repeating unit sequence and dense triple-helix structure of the collagen, only a few proteases have a capability of catalyzing hydrolysis of the bone collagen, and there are few collagenases and producing strains on the market at present. There are studies showing that *Clostridium histolyticum, Bacillus* sp., *Candida albicans* and *Vibrio vulnificus* have potentials to produce collagenases, but most of these strains are pathogenic bacteria. When producing collagenases, the pathogenic bacteria also produce corresponding toxins, so these strains are not suitable for preparing bone-derived foods.

SUMMARY

One object of the present disclosure is to provide a gene recombinant vector, a genetically engineered strain and a preparation method of a collagenase. The collagenase is capable of degrading a bone collagen, and improving a yield of a low-molecular-weight bone collagen peptide.

In order to achieve these objects and other advantages according to the present disclosure, a gene recombinant vector of a collagenase is provided, which comprises a collagenase gene, wherein an amino acid sequence of a collagenase encoded by the collagenase gene is shown in SEQ ID NO. 1.

Preferably, for the gene recombinant vector of the collagenase, a DNA sequence of the collagenase gene is shown in SEQ ID NO. 2, and a cDNA sequence of the collagenase gene is shown in SEQ ID NO. 4.

The present disclosure further provides a genetically engineered strain of a collagenase, which comprises the gene recombinant vector of the collagenase above.

The present disclosure further provides a preparation method of a collagenase, which comprises the following steps of:
- S1: extracting a RNA sequence of a host strain *Rhizopus oryzae* CGMCC3.17463, obtaining a cDNA sequence of the host strain by reverse transcription, performing PCR amplification with the cDNA sequence of the host strain as a template to obtain a cDNA sequence of the collagenase, and then linking the cDNA sequence of the collagenase to a *Pichia pastoris* expression vector pPIC9 to obtain a gene recombinant vector of the collagenase;
- S2: transforming the gene recombinant vector of the collagenase into a host cell of a *Pichia pastoris* Gs115 to obtain a genetically engineered strain of the collagenase;
- S3: activating the genetically engineered strain of the collagenase, then culturing the genetically engineered strain of the collagenase at 30° C. for 2 days to 3 days, and inducing the genetically engineered strain of the collagenase with methanol to express and produce a crude enzyme solution of the collagenase; and
- S4: concentrating and purifying the crude enzyme solution to obtain the purified collagenase.

Preferably, for the preparation method of the collagenase, in step S1, the performing the PCR amplification with the cDNA sequence of the host strain as the template to obtain the cDNA sequence of the collagenase specifically comprises the following steps of:
- S1a: designing and synthesizing a specific primer pair RoAPA_F and RoAPA_R of the collagenase, wherein a sequence of the RoAPA_F is shown in SEQ ID NO. 5, and a sequence of the RoAPA_R is shown in SEQ ID NO. 6; and
- S1b: performing PCR amplification with the cDNA of the host strain obtained by reverse transcription as the template and the RoAPA_F and the RoAPA_R as primers to obtain the cDNA sequence of the collagenase.

Preferably, for the preparation method of the collagenase, in step S1, conditions for performing the PCR amplification with the cDNA sequence of the host strain as the template to obtain the cDNA sequence of the collagenase are 97° C. for 3 minutes; 95° C. for 30 seconds, 63° C. for 30 seconds and 72° C. for 1 minute, in 32 cycles; and 72° C. for 10 minutes.

The present disclosure at least comprises the following beneficial effects.

Firstly, in the present disclosure, a new collagenase with a collagen hydrolysis activity is explored, and an encoding gene of the collagenase is introduced into the engineered strain by a biological enzyme engineering method, so as to implement heterologous expression of the collagenase, and promote industrial production of a bone collagenase.

Secondly, during enzymatic preparation of a bone collagen peptide, the collagenase provided by the present disclosure is capable of improving a yield of a low-molecular-weight bone collagen peptide.

Other advantages, objects and features of the present disclosure will be partially reflected by the following description, and will be partially understood by those skilled in the art through researching and practicing the present disclosure.

DETAILED DESCRIPTION

Figure 1:
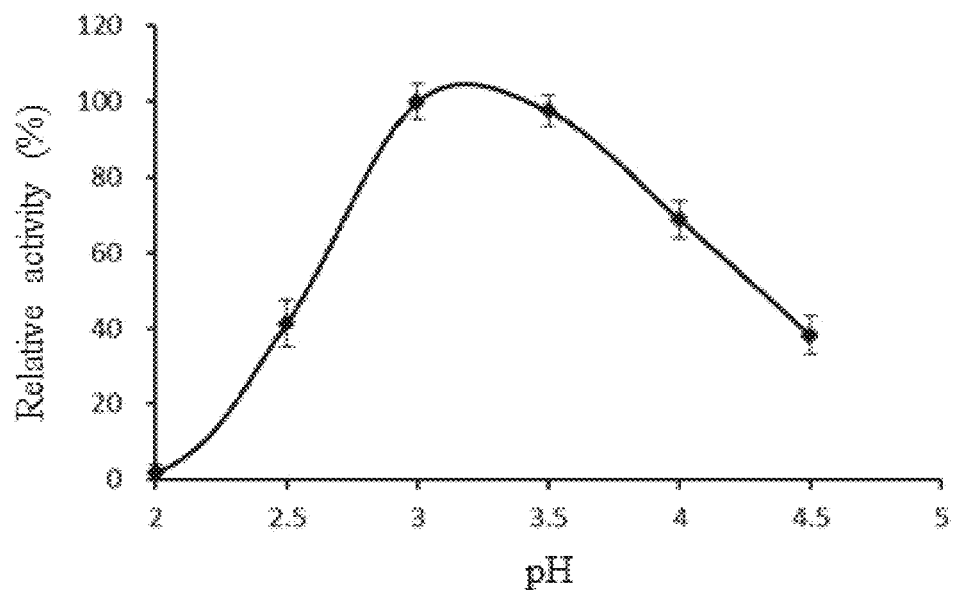
FIG. 1 is a curve chart of relative enzyme activities of a collagenase RoAPA under different pH conditions according to one of the technical solutions of the present disclosure.

The present disclosure is further described in detail with reference to the accompanying drawings, so that those skilled in the art are able to implement according to the text of the specification.

It should be understood that the terms such as "have", "contain" and "comprise" used herein do not indicate the existence or addition of one or more other elements or combinations thereof.

Test Materials and Reagents

1. Strains and vectors: a host strain is *Rhizopus oryzae*, which may be obtained from China General Microbiological Culture Collection Center (CGMCC) and numbered as CGMCC 3.17463; an engineered strain is *Pichia pastoris* GS115, which is used for heterologous expression of protein and purchased from Sangon Biotech (Shanghai) Co., Ltd.; and a *Pichia pastoris* expression vector pPIC9 purchased from Invitrogen Company.

2. Enzymes and other biochemical reagents: an endonuclease is purchased from TaKaRa Company, a ligase is purchased from Invitrogen Company, and others are all domestic reagents (all commercially available from biochemical reagent companies).

3. *Escherichia coli* medium: 1% of yeast extract, 2% of peptone, 1.34% of YNB, 0.000049<Biotin, and 1% of glycerol (v/v/v).

4. BMGY medium; 1% of yeast extract, 2% of peptone, 1.34% of YNB, 0.000049<Biotin, and 1% of glycerol (v/v).

5. BMMY medium: except for the glycerol replaced by 0.5% of methanol, other ingredients are the same as those of the BMGY, with a pH of 4.0.

Note: molecular biology experimental methods unspecified in the following embodiments are all implemented according to specific methods listed in the book *Molecular Cloning: a Laboratory Manual* (Fourth Edition) written by J. Sambrook, or implemented according to instructions of kits and products.

Embodiment

A DNA sequence of a host strain *Rhizopus oryzae* CGMCC3.17463 was extracted and stored at −20° C. Specific primers RoAPA_F and RoAPA_R for gene cloning of the collagenase RoAPA were designed, sequences of the primers RoAPA_F and RoAPA_R were respectively shown in SEQ ID NO. 5 and SEQ ID NO. 6, and PCR amplification was performed with the DNA sequence of the host strain *Rhizopus oryzae* CGMCC3.17463 as a template, wherein amplification conditions were: 97° C. for 3 minutes; 95° C. for 30 seconds, 63° C. for 30 seconds and 72° C. for 1 minute, in 32 cycles; and 72° C. for 10 minutes. A DNA sequence of about 1252 bp was obtained, and the DNA sequence was recycled and sent to Shanghai Majorbio Bio-pharm Technology Co., Ltd. for sequencing, with a gene sequence shown in SEQ ID NO. 2. This DNA sequence was the DNA sequence of the collagenase RoAPA, and a corresponding amino acid sequence was shown in SEQ ID NO. 1.

2. Obtaining of cDNA Sequence of Collagenase RoAPA

A RNA sequence of the host strain *Rhizopus oryzae* CGMCC3.17463 was extracted, and then a cDNA sequence of the host strain *Rhizopus oryzae* CGMCC3.17463 was obtained by reverse transcription. Cloning primers RoAPA_F and RoAPA_R were designed, the sequences of the primers RoAPA_F and RoAPA_R were respectively shown in SEQ ID NO. 5 and SEQ ID NO. 6, and PCR amplification was performed with the cDNA sequence of the host strain *Hizopus oryzae* CGMCC3.17463 as a template. The cDNA sequence of the collagenase RoAPA was obtained after amplification, and the sequence obtained after amplification was sent to Shanghai Majorbio Bio-pharm Technology Co., Ltd. for sequencing, with a length of 1194 bp and a gene sequence shown in SEQ ID NO. 4.

Information of the DNA sequence of the collagenase RoAPA and information of the cDNA sequence of the collagenase RoAPA were analyzed. The DNA sequence of the collagenase RoAPA had a full length of 1252 bp, one intron with a length of 58 bp, and a base sequence shown in SEQ ID NO. 3. An amino acid sequence deduced from the cDNA sequence of the collagenase RoAPA was predicted by software, finding that 21 amino acids at an N-terminal were a signal peptide sequence of a protein. It was found from Blast comparison that a highest similarity between a protein sequence of the collagenase RoAPA and a protease sequence published in a database was only 78.6%, and a highest similarity between the protein sequence of the collagenase RoAPA and a sequence of a related enzyme reported in an existing crystal structure was only 51.3%. The results above show that a protease encoding gene separated and cloned from the host strain *Rhizopus oryzae* CGMCC3.17463 has a high novelty.

3. Obtaining of Recombinant Engineered Strain (1) Preparation of Recombinant Engineered Strain Primers RoAPA_F and RoAPA_R with EcoR I and Not I restriction sites were designed and synthesized with the correctly sequenced cDNA of the collagenase RoAPA as the template, and sequences of the primers RoAPA_F and RoAPA_R were respectively SEQ ID NO. 5 and SEQ ID NO. 6, wherein an underlined part of the sequence of the primer RoAPA_F (CGGAATTCATGAAATTCACTCTTGTCTCTT) was the EcoR I restriction site, and an underlined part of the sequence of the primer RoAPA_R (TTGCGGCCGCTTATTTGTTTTGGTCAACAGAAGC) was the Not I restriction site. PCR amplification was performed with the cDNA of the collagenase RoAPA as the template and the RoAPA_F and the RoAPA_R as primers, then a PCR product was digested with the EcoR I and the Not I to obtain the amplified cDNA sequence of the collagenase RoAPA, and the amplified cDNA sequence of the collagenase RoAPA was linked to a *Pichia pastoris* expression vector pPIC9 to obtain a recombinant expression vector pPIC9-RoAPA. In other words, the cDNA sequence of the collagenase RoAPA was inserted into a downstream of a signal peptide sequence of the expression vector above, so as to form a correct reading frame with the signal peptide, and construct the *Pichia pastoris* expression vector pPIC9-

RoAPA, which was then transformed into a competent cell Trans1 of *Escherichia coli* in an *Escherichia coli* medium. DNA sequencing was performed on positive transformants, and the correctly sequenced transformants were used for preparing a large number of recombinant plasmids. A DNA sequence of an expression plasmid vector was linearized with a restriction endonuclease Bgl II, competent cells of a *Pichia pastoris* GS115 were transformed by electric shock, and cultured at 30° C. for 2 days to 3 days, and transformants grown on an MD plate were selected for further expression experiment. Specific operations were referred to a *Pichia pastoris* expression operation manual. Moreover, an expression vector containing the cDNA sequence of the signal peptide sequence of the collagenase RoAPA was constructed and transformed in the same way.

(2) Screening of Transformants with High Collagenase Activity

A plurality of single colonies were selected from the MD plate on which the transformants grew by a sterilized toothpick, and touched on another MD plate according to numbers, and the MD plate was placed in an incubator at 30° C. for culture for 1 day to 2 days until the colonies grew out. The transformants were selected from the MD plate according to numbers, correspondingly inoculated into a centrifuge tube containing 3 mL of BMGY medium respectively, and cultured in a shaking table for 48 hours at 30° C. and 220 rpm. A bacterial solution cultured in the shaking table for 48 hours was centrifuged at 3,000×g for 15 minutes, a supernatant was removed, and then 1 mL of BMMY medium containing 0.5% of methanol was added into the centrifuge tube, and induced and cultured at 30° C. and 220 rpm. After induction and culture for 48 hours, the solution was centrifuged at 3,000×g for 5 minutes, a supernatant was taken for enzyme activity detection, and transformants with high collagenase activity were screened out. Specific operations were referred to the *Pichia pastoris* expression operation manual.

4. Preparation of Recombinant Collagenase RoAPA (1) Expression of Recombinant Engineered Strain pPIC9-RoAPA The transformants with high enzyme activity were screened out, inoculated in 300 mL of BMGY liquid medium, and shakily cultured in a shaking table for 48 hours at 30° C. and 220 rpm. After shaking culture in the shaking table, the solution was centrifuged at 5,000 rpm for 5 minutes, a supernatant was removed, and then 100 mL of BMMY liquid medium containing 0.5% of methanol was added into bacteria, and induced and cultured at 30° C. and 220 rpm for 72 hours. During induction and culture, a methanol solution was added once every 24 hours to compensate for a loss of the methanol, so that a concentration of the methanol was kept at about 0.5%. After induction and culture for 72 hours, the solution was centrifuged at 12,000×g for 10 minutes, a supernatant fermentation broth was collected, and enzyme activity detection and SDS-PAGE protein electrophoresis analysis were performed.

(2) Obtaining of Recombinant Collagenase RoAPA by Purification

A supernatant of a collagenase of a recombinant engineered strain expressed in a shake flask was collected, and concentrated by 10 kDa membrane package. Meanwhile, the medium therein was replaced by a low-salt buffer solution, and then further concentrated by 10 kDa ultrafiltration tube. The recombinant collagenase RoAPA capable of being diluted to a certain multiple was concentrated, and then purified by ion exchange chromatography to obtain the recombinant collagenase RoAPA. Specifically, 2.0 mL of concentrated solution of the recombinant collagenase RoAPA was taken to pass through a HiTrap Q Sepharose XL anion column pre-balanced with 20 mM Tris-HCl (pH 7.5), then linear gradient elution was performed with 0.1 mol/L NaCl, and enzyme activity detection and protein concentration determination were performed on an eluate collected step by step.

5. Analysis on Some Performances of Collagenase RoAPA

An activity of the collagenase RoAPA prepared by the present disclosure was analyzed by a foline-phenol reagent development method. A specific method was as follows: after the collagenase RoAPA reacted with 1 mL of reaction system for 10 minutes, 1 mL of trichloroacetic acid (0.4 mol/L) was added to terminate the reaction, wherein the 1 mL of reaction system had a pH of 3.0 and a temperature of 30° C., and contained 500 µL of appropriate diluted enzyme solution and 500 µL of substrate. After terminating the reaction, the reaction system was centrifuged at 12,000 rpm for 3 minutes, and 500 µL of supernatant was sucked, added with 2.5 mL of sodium carbonate (0.4 mol/L), then added with 500 µL of foline-phenol reagent, and developed at 40° C. for 20 minutes. After cooling, an OD value was determined at an ultraviolet wavelength of 680 nm. Definition of protease activity unit: under certain conditions, an amount of enzyme needed to decompose a substrate casein to produce 1 µmol tyrosine per minute was one activity unit (U).

(1) Detection of Optimum pH and pH Stability of Collagenase RoAPA

The collagenase RoAPA purified by the present disclosure was subjected to an enzymatic reaction under different pH conditions to determine an optimum pH value. The used buffer solution comprised a glycine-hydrochloric acid buffer solution with a pH of 2.0 to 3.0, a citric acid-disodium hydrogen phosphate series buffer solution with a pH of 3.0 to 8.0 and a Tris-HCl series buffer solution with a pH of 8.0 to 10.0. Optimum pH values of the purified collagenase RoAPA in different pH buffer systems at 55° C. were determined. The results are shown in FIG. 1: the optimum pH of the collagenase RoAPA at 55° C. is 3.0, and the enzyme can maintain a high enzyme activity at a pH ranging from 3.0 to 4.0.

Figure 2:
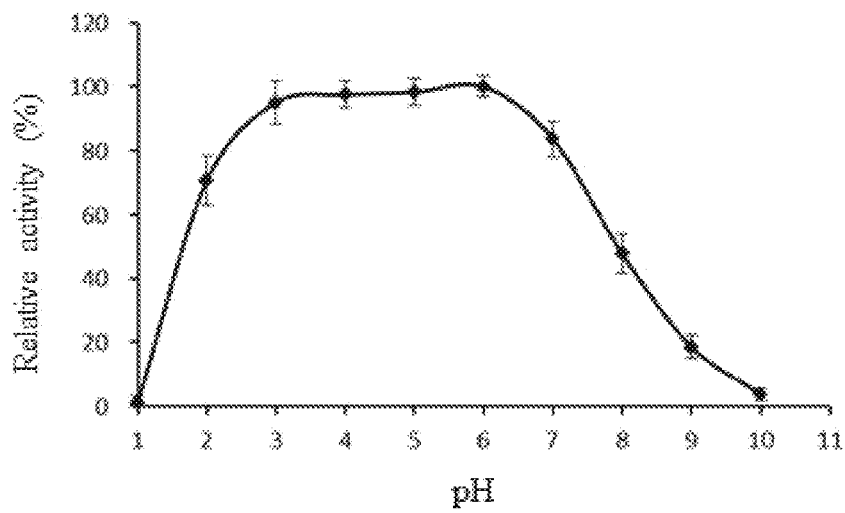
FIG. 2 is a curve chart of a pH stability of the collagenase RoAPA according to one of the technical solutions of the present disclosure.

The enzyme solution was processed in buffer solutions with different pH values at 30° C. for 60 minutes, and then an enzyme activity was determined to study a pH stability of the enzyme. The results are shown in FIG. 2, and the results show that: the collagenase RoAPA can maintain more than 90% enzyme activity at a pH ranging from 3.0 to 6.0, which indicates that the enzyme has a good pH stability under an acidic condition.

Figure 3:
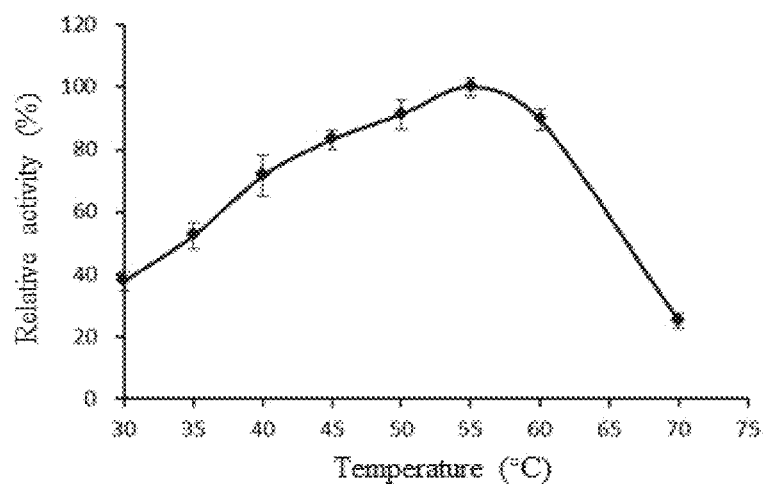
FIG. 3 is a curve chart of relative enzyme activities of the collagenase RoAPA at different temperatures according to one of the technical solutions of the present disclosure.
Figure 4:
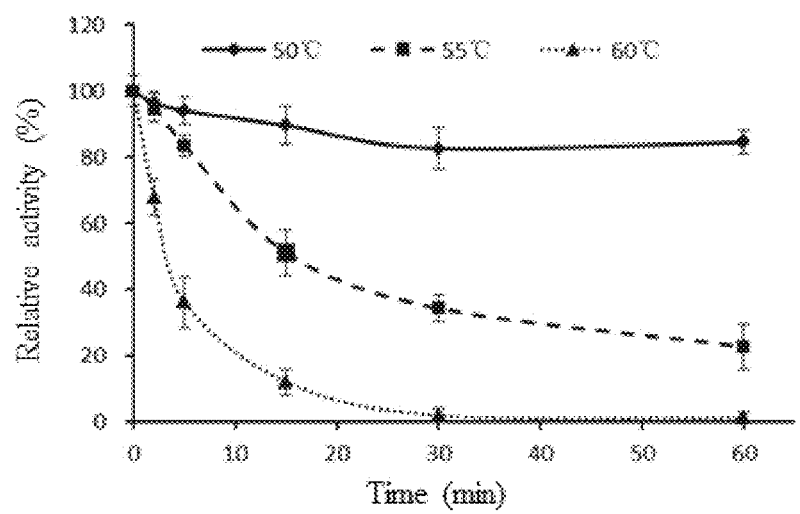
FIG. 4 is a curve chart of a temperature stability of the collagenase RoAPA according to one of the technical solutions of the present disclosure.

(2) Detection of Optimum Reaction Temperature and Thermal Stability of Collagenase RoAPA Enzyme activities of the purified collagenase RoAPA at different temperatures (30° C. to 70° C.) under pH 3.0 were determined. Results are shown in FIG. 3: the optimum reaction temperature of the enzyme is 55° C., and the enzyme still has more than 80% enzyme activity at 60° C. The purified collagenase RoAPA was processed at 50° C., 55° C. and 60° C. for different times respectively, and then enzyme activities of the collagenase RoAPA were determined at 55° C. Results are shown in FIG. 4: processing the collagenase RoAPA at 60° C. for 30 minutes can completely inactivate the protein. To sum up, the collagenase RoAPA has a high protein hydrolysis activity at 50° C. to 60° C., and the protease can be completely inactivated by incubation at 60° C. for 30 minutes. This means that the protease of the present disclosure has an important value in use in the fields of foods and medicines.

Figure 5:
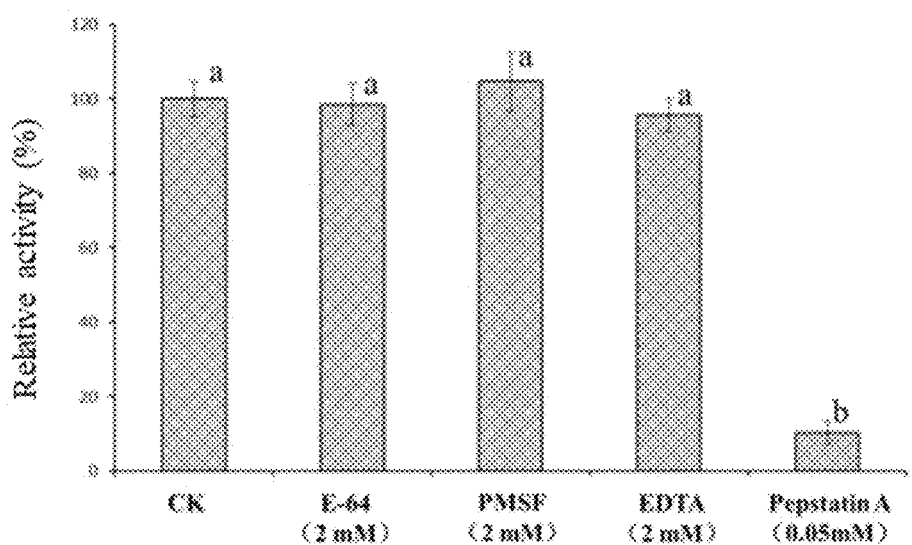
FIG. 5 shows influences of different inhibitors on a catalytic activity of the RoAPA according to one of the technical solutions of the present disclosure.

(3) Influences of Different Metal Ions/Reagents on Activity of Collagenase RoAPA In order to determine influences of different metal ions on the activity of the collagenase RoAPA, before determining a catalytic activity of the collagenase RoAPA, different metal ions such as $Mn^{2+}$, $Cu^{2+}$, $Cr^{3+}$, $Zn^{2+}$, $K^+$, $Na^+$, $Ca^{2+}$, $Mg^{2+}$, $Ni^{2+}$, $Co^{2+}$, $Pb^{2+}$ and $Fe^{3+}$ were added into the reaction system, a final concentration was controlled to be 3 mM, and a pH of the solution was adjusted to be 3.0. Then, a protease activity was determined at 55° C. The results show that $Mn^{2+}$ and $Cu^{2+}$ can obviously activate the collagenase RoAPA, $Pb^{2+}$ and $Fe^{3+}$ can obviously inhibit a proteolysis activity of the collagenase RoAPA, and other metal ions have little influence on the activity of the collagenase RoAPA. Meanwhile, we analyzed influences of addition of different protease inhibitors (blank control CK, 2 mM cysteine protease inhibitor E-64, 2 mM serine protease inhibitor PMSF, 5 mM metalloprotease inhibitor EDTA, and 0.05 mM aspartic protease inhibitor Pepstatin A) on the activity of the collagenase RoAPA. The results are shown in FIG. 5. Studies show that the collagenase RoAPA can be specifically inhibited by the Pepstatin A, and the Pepstatin A can be specifically bound to a catalytic pocket of an aspartic protease but not cleaved, thus inhibiting an activity of a catalytic residue, which further proves that the collagenase RoAPA belongs to an aspartic protease family.

Figure 6:
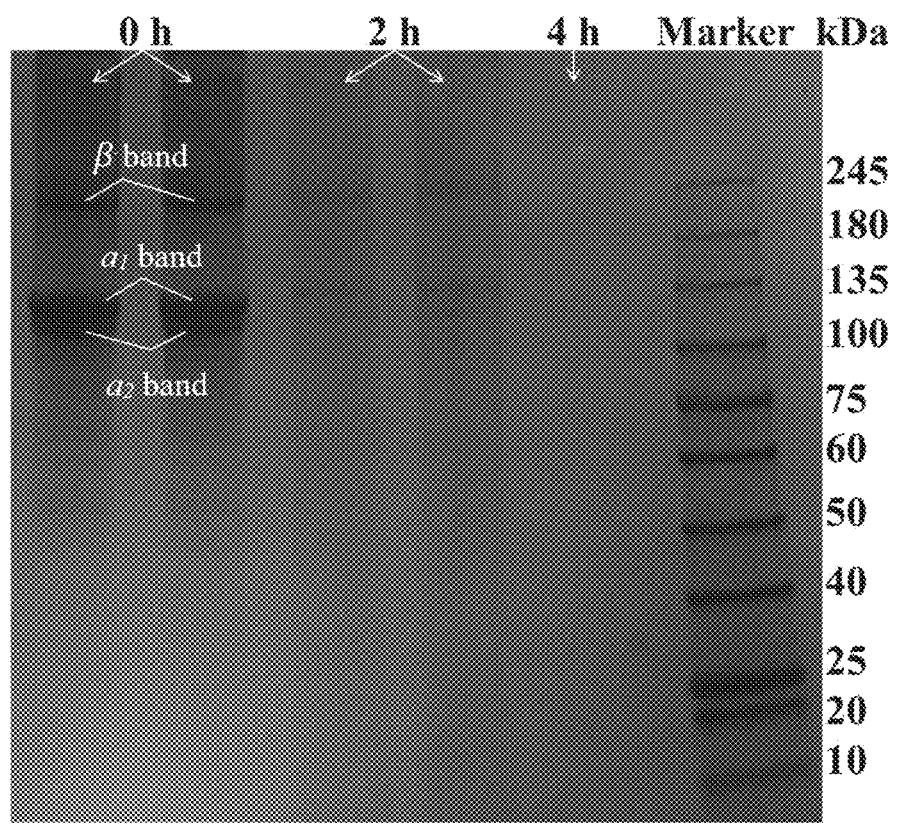
FIG. 6 is a SDS-PAGE analysis diagram of using the RoAPA to hydrolyze a bone collagen according to one of the technical solutions of the present disclosure.

6. Application of Collagenase RoAPA in Preparing Low-Molecular-Weight Bone Collagen Peptide (1) Enzymolysis of Bone Collagen 5.0 g of bone collagen were accurately weighed and added with 1,000 mL of water to prepare 0.5% (w/v) bone collagen solution. A pH of the solution was adjusted to be 3.5, added with the collagenase RoAPA according to an addition amount of 5,000 U/g, and stirred evenly, and an enzymolysis reaction was performed at 50° C. After finishing the reaction, the solution was heated in boiling water bath for 10 minutes to completely inactivate the collagenase RoAPA. 0.25 mL of bone collagen enzymatic hydrolysate was mixed with equal volume of 10% TCA, shaken evenly, and centrifuged at 10,000 g and 4° C. for 20 minutes. 50 μL of supernatant was sucked out, added into a 96-well plate in sequence, then added with 200 μL of BCA working solution in sequence, and incubated at room temperature for 2 hours. The mixture was placed in a microplate reader, and an absorbance was determined at a wavelength of 562 nm. Studies show that with extension of enzymolysis time, a degree of hydrolysis is gradually increased, a plateau period is reached after about 4 hours, and then the degree of hydrolysis is no longer increased with extension of time. The above results indicate that the collagenase RoAPA can catalyze hydrolysis of the bone collagen under an acidic condition. Polyacrylamide gel electrophoresis (SDS-PAGE) analysis was performed on a bone collagen hydrolysate. The results show that a molecular weight of the bone collagen hydrolyzed by the collagenase RoAPA is decreased obviously, and characteristic bands ($\alpha_1$ and $\alpha_2$ bands) of the bone collagen gradually disappear with extension of reaction time (FIG. 6). The above results indicate that the collagenase RoAPA can catalyze the hydrolysis of the bone collagen to produce a small-molecular peptide, thus having an application potential of industrial preparation of the bone collagen peptide.

(2) Determination of Molecular-Weight Distribution of Bone Collagen Enzymatic Hydrolysate An Agilent HPLC1260-II system (Agilent Technologies Inc., California, USA) was used to determine molecular-weight distribution of the bone collagen hydrolysate. A TSK gel G2000 SWXL chromatographic column (7.8 mm×300 mm, TOSOH, Tokyo, Japan) was used; a column temperature was 40° C.; a mobile phase was A, which was 45% (v/v) of acetonitrile solution mixed with 0.1% of trifluoroacetic acid; equal gradient elution was performed; a flow rate was 0.5 mL/min; and an injection volume was 10 μL, and a response value was determined at a wavelength of 214 nm. Gly-Sar (146 Da), Gly-Gly-Tyr-Arg (451 Da), Bacitracin (1,422 Da), Aprotinin (6,511 Da) and Cytochrome C (12,327 Da) were used as standard products, and a standard curve between a retention time (X) and a molecular-weight logarithm (Y) was established ($Y=-3.9331X+27.517$, $R2=0.987$). Table 1 shows the molecular-weight distribution of the bone collagen peptide prepared by hydrolyzing the bone collagen with the collagenase RoAPA. From this, it can be seen that the collagen peptide hydrolyzed with the collagenase RoAPA has more advantages in molecular-weight distribution in comparison to a pepsin and a trypsin, and both a distribution sum of the molecular weight less than 1,000 Da and a distribution sum of molecular weight less than 2,000 Da are highest. It is found from analysis of a free amino acid content of the bone collagen enzymatic hydrolysate that free amino acids produced by hydrolyzing the bone collagen with the collagenase RoAPA account for about 6.53%, which is lower than ratios of free amino acids in pepsin and trypsin enzymatic hydrolysates, indicating that the RoAPA hydrolysate of the bone collagen mainly exists in a form of peptide.

TABLE 1

Molecular-weight distribution of bone collagen peptide prepared by enzymolysis method

| Molecular weight (Da) | RoAPA | Pepsase | Trypsase |
|---|---|---|---|
| >10000 | 0.17 | 0.31 | 0.25 |
| 5000 to 10000 | 1.47 | 2.79 | 3.58 |
| 2000 to 5000 | 11.91 | 18.83 | 17.13 |
| 1000 to 2000 | 23.92 | 25.38 | 23.68 |
| 500 to 1000 | 34.66 | 32.84 | 30.63 |
| 180 to 500 | 21.34 | 12.13 | 14.96 |
| <180 | 6.53 | 7.72 | 9.77 |

Although the implementation of the present disclosure has been disclosed above, the present disclosure is not limited to the applications listed in the specification and the embodiments. The present disclosure can be applied to various fields suitable for the present disclosure absolutely, and other modifications can be easily realized by those skilled in the art. Therefore, the present disclosure is not limited to the specific details and the embodiments shown and described herein without departing from the general concepts defined by the claims and equivalent scopes.

What is claimed is:

1. A cDNA having the nucleic acid sequence of SEQ ID NO. 4.

2. The cDNA according to claim 1, wherein the cDNA is cloned into an expression vector that is transformed into a host cell to express a protein that has the amino acid sequence of SEQ ID NO. 1.

3. The cDNA according to claim 1, wherein the cDNA is obtained by a reverse transcription PCR with a pair of primers having the nucleic acid sequences of SEQ ID NO. 5 and SEQ ID NO. 6 from total RNAs isolated from *Rhizopus oryzae* CGMCC3.17463.

4. The cDNA according to claim 2, wherein the expression vector is a *Pichia pastoris* expression vector pPIC9, the host cell is *Escherichia coli.*

5. The cDNA according to claim 2, wherein the protein has activity of collagenase.

* * * * *